United States Patent [19]

Carlson

[11] Patent Number: 4,700,711
[45] Date of Patent: Oct. 20, 1987

[54] ULTRASONIC DETECTOR WITH INTEGRAL CONFIDENCE TESTS

[75] Inventor: David L. Carlson, Ames, Iowa

[73] Assignee: Renco Corporation, Minneapolis, Minn.

[21] Appl. No.: 801,080

[22] Filed: Nov. 22, 1985

[51] Int. Cl.⁴ ............................................. A61B 10/00
[52] U.S. Cl. ...................................... 128/660; 73/612
[58] Field of Search .............. 128/660; 73/1 DV, 609, 73/610, 612, 614

[56] References Cited

U.S. PATENT DOCUMENTS

| | | | |
|---|---|---|---|
| 3,872,858 | 3/1975 | Hudson et al. | 128/660 |
| 3,954,098 | 5/1976 | Dick et al. | 128/660 |
| 4,106,346 | 8/1978 | Matzuk | 128/660 |
| 4,112,927 | 9/1978 | Carlson . | |
| 4,138,999 | 2/1979 | Eckhart et al. . | |
| 4,226,229 | 10/1980 | Eckhart et al. . | |
| 4,240,281 | 12/1980 | Lather et al. | 73/1 DV |
| 4,261,367 | 4/1981 | Freese | 128/660 |
| 4,359,055 | 11/1982 | Carlson . | |
| 4,359,056 | 11/1982 | Carlson . | |
| 4,373,527 | 2/1983 | Fischell | 128/903 |
| 4,465,077 | 8/1984 | Schneider | 128/738 |
| 4,603,702 | 8/1986 | Hwang et al. | 128/660 |

Primary Examiner—Kyle L. Howell
Assistant Examiner—Ruth S. Smith
Attorney, Agent, or Firm—Merchant, Gould, Smith, Edell, Welter & Schmidt

[57] ABSTRACT

An ultrasonic sounding apparatus is described for measuring backfat and determining pregnancy in animals, having a plurality of self-test features to ensure integrity of the measurements. In the preferred embodiment, a hand-held ultrasonic device is described for detecting increased amounts of amniotic fluid in an animal's uterus for an indication of pregnancy. Every two and one half seconds the hand-held ultrasonic device emits a small tone indicating that the transducer is in correct contact with the body of the animal. The generation of this skin contact tone is performed using the same ultrasonic circuitry that is used to detect the amniotic fluid, thereby providing the dual function of circuit self-test and skin contact test. In addition, the device includes a power-up confidence test to test the components of the circuit and indicate by an audible tone that everything is working properly. This power-up confidence test also uses the same ultrasonic circuitry that performs the detection of amniotic fluid. Included in this invention is a battery check that is also performed on power-up.

8 Claims, 3 Drawing Figures

- A BURST CYCLE TIMER
- B PULSE GENERATOR
- C SENSITIVITY CONTROL
- D AMPLIFIER OUTPUT
- E THRESHOLD DETECTOR
- F INHIBIT CONTROL
- G BLANKING GATE OUTPUT
- H AUDIO TONE OUTPUT

ULTRASONIC DETECTOR WITH INTEGRAL CONFIDENCE TESTS

BACKGROUND OF THE INVENTION

The present invention relates generally to ultrasonic detection systems, and in particular to the field of biological detection using ultrasonic frequencies.

Ultrasonic frequencies have been used in a number of prior art systems for the detection of material density interfaces in fluid bodies. Ultrasonic devices operate on the theory that material interfaces can be detected by the reflection of sonic or ultrasonic frequencies. An ultrasound device will emit a burst of energy at a specific frequency and then monitor the fluid body for echoes reflected off the density interfaces. The distance at which the reflected surface is located from the ultrasound device can be calculated by the velocity of the emitted frequency through the fluid multiplied by the time between the energy burst and the reception of the reflected echo. These echo patterns can also be analyzed to determine attributes of the reflecting body such as its density by observing the energy strength of the reflected echo.

The concept of ultrasonic detection has been used with success in several areas of the medical industry. Ultrasonic transducers and detectors placed on the skin of a patient can provide valuable data on the functioning and location of internal organs of the body through non-invasive means. Ultrasonic detection in the monitoring of human pregnancies, for instance, has proven to be a safe and effective medical tool that allows a doctor to check on the progress of a fetus without the use of harmful radiation as in X-rays.

Another use of ultrasonic detection means has been in the field of animal husbandry. Ultrasonic detectors have been used as valuable tools both in the field of veterinary science and animal breeding. Very accurate information on the health and progress of farm animals can be determined from telltale ultrasonic reflection signatures which are common among animals of common breeds. For example, ultrasonic pulsing and detection has been used for detecting pregnancies in farm animals, since the buildup of amniotic fluid in the enlarged uterus of a pregnant farm animal provides a very distinct echo pattern.

Another use of ultrasonic detectors in the field of animal husbandry has been the calculation of the amount of backfat on hogs. The calculation of the distance between reflected echoes has been used to distinguish between various layers of tissue and fat for the grading of hogs. This alternative ultrasonic grading technique has been widely adopted due to the more humane treatment of animals by using non-invasive techniques to check the quality of the hogs.

Prior art ultrasonic detectors, whether used for checking for animal pregnancy or for checking depth of backfat, have used various indicator techniques to alert the operator of the presence or absence of the sought quality in the animal. Visual and audible indicators that have been used include alert buzzers, cathode ray tube displays and digital numeric readouts. These various ultrasonic detector devices have all suffered from common problems due to the harsh operating conditions of the environment in which they are used. Erroneous readings may result from the misuse or mishandling of the ultrasonic devices which leads to a breakdown in the confidence of their operation. Such problems include the poor contact of the ultrasound transducer to the body of the animal, the failure of internal electronic components of the ultrasound circuits, and the use of partially exhausted batteries within the circuits.

The present invention overcomes the shortcomings of these prior art ultrasound detection devices by providing for power-on confidence testing of the entire circuit to check out the individual circuit components and verify the correct functioning with an audible tone. The present invention also continuously monitors the skin contact between the ultrasound transducer and the skin of the animal being monitored. The present invention also includes a continuous battery check to indicate when the battery falls below an acceptable operating threshold voltage.

SUMMARY OF THE INVENTION

An object of the present invention is to provide an improved ultrasonic detection device which provides for increased confidence in its accuracy. The present invention is adaptable for use in determining pregnancy in sows, for measuring backfat on hogs, and other ultrasonic applications.

A further object of the present invention is to provide an ultrasonic detection device which continually monitors the skin contact of the detection transducer and reports the quality of the contact to the user of the device.

A further object of the present invention is to provide an ultrasound detection device which performs a self-test upon initial power-up and reports the success of this test to the user of the device.

A further object of the present invention is to provide an ultrasound detection device which continually monitors the condition of the batteries and reports a weakened condition to the user.

In the preferred embodiment of the present invention, an ultrasonic device with an integral transducer is placed in contact with the belly of the sow for use in detecting increased amounts of amniotic fluid in the sow's uterus, which would indicate pregnancy. The device is a hand-held electronic module which determines the sow's pregnancy based on the power of the reflected signature of the ultrasound burst. A correct ultrasound signature indicating pregnancy will cause an audible signal to be emitted from the hand-held device, alerting the user that a positive pregnancy has been identified. Every two and one-half seconds the hand-held ultrasonic detection device emits a small tone indicating the transducer is in correct contact with the body of the animal. The absence of this tone every two and one-half seconds indicates that the transducer is misaligned with the body of the animal, which would indicate possible incorrect readings from the ultrasound device. In addition, when the device is powered up, a built-in confidence test is performed to check out the components of the circuit and indicate by an audible tone that everything is working properly. The battery of the hand-held device is continually checked while the device is operating and will indicate by an audible tone if the battery voltage has dropped below an acceptable threshold.

BRIEF DESCRIPTION OF THE DRAWINGS

In the drawings of the preferred embodiment of the present invention, wherein like numerals refer to like elements throughout the several views.

DESCRIPTION OF THE PREFERRED EMBODIMENT

For purposes of this description, the preferred embodiment of the present invention is an improved ultrasonic detection device for use in determining the pregnancy of sows. It will be appreciated by those skilled in the art that the present invention is adaptable for use in ultrasonic backfat meters or in other applications for both human and animal use in detecting various physiological features through the non-invasive technique of ultrasound.

Figure 1:
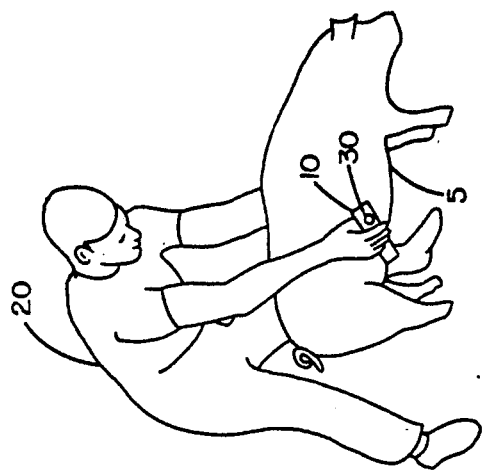
FIG. 1 is a pictorial diagram illustrating the operation of the ultrasonic detector device.

Referring to FIG. 1, the field use of an ultrasonic detector including the present invention is depicted. The ultrasonic detector is comprised of the electronic circuits and ultrasonic transducer contained in housing 10. The housing for the ultrasonic circuits is small enough to be held in one hand by the user 20 and positioned on the skin of the sow 5 on the underside near the uterus. It will be appreciated by those skilled in the art that the transducer need not be made an integral part of the device housing, but could be placed, for example, at the end of a remote transducer housing. The hand-held ultrasonic detection apparatus 10 is operated by means of a push-button switch 30 which activates the device. When power is applied to the circuit a power-on confidence test is performed, the success of which is indicated by a small audible chirp through a piezoelectric sounder. Thereafter, the device continually checks the voltage level of the battery to ensure that the operating voltage is maintained above an acceptable level. If the battery voltage should fall below an acceptable level, another audible tone would be heard on the piezoelectric sounder.

In addition, the electronic circuits of the ultrasonic detection device continually check the contact between the ultrasonic transducer and the skin of the sow every two and one-half seconds. Another audible chirp is heard every two and one-half seconds indicating that good contact is continually being maintained. If the ultrasonic detection device receives an echo from the amniotic fluid in the uterus of the sow strong enough to indicate pregnancy, an extended tone will be heard by the user on the piezoelectric sounder indicating a positive pregnancy identification. If no echo is received from the ultrasonic detection device, no audible tones will be heard by the user except for the skin contact chirp which will be heard every two and one-half seconds. If no audible tone indicating pregnancy is heard for a period of time, the user may conclude that the sow is not pregnant.

Figure 2:
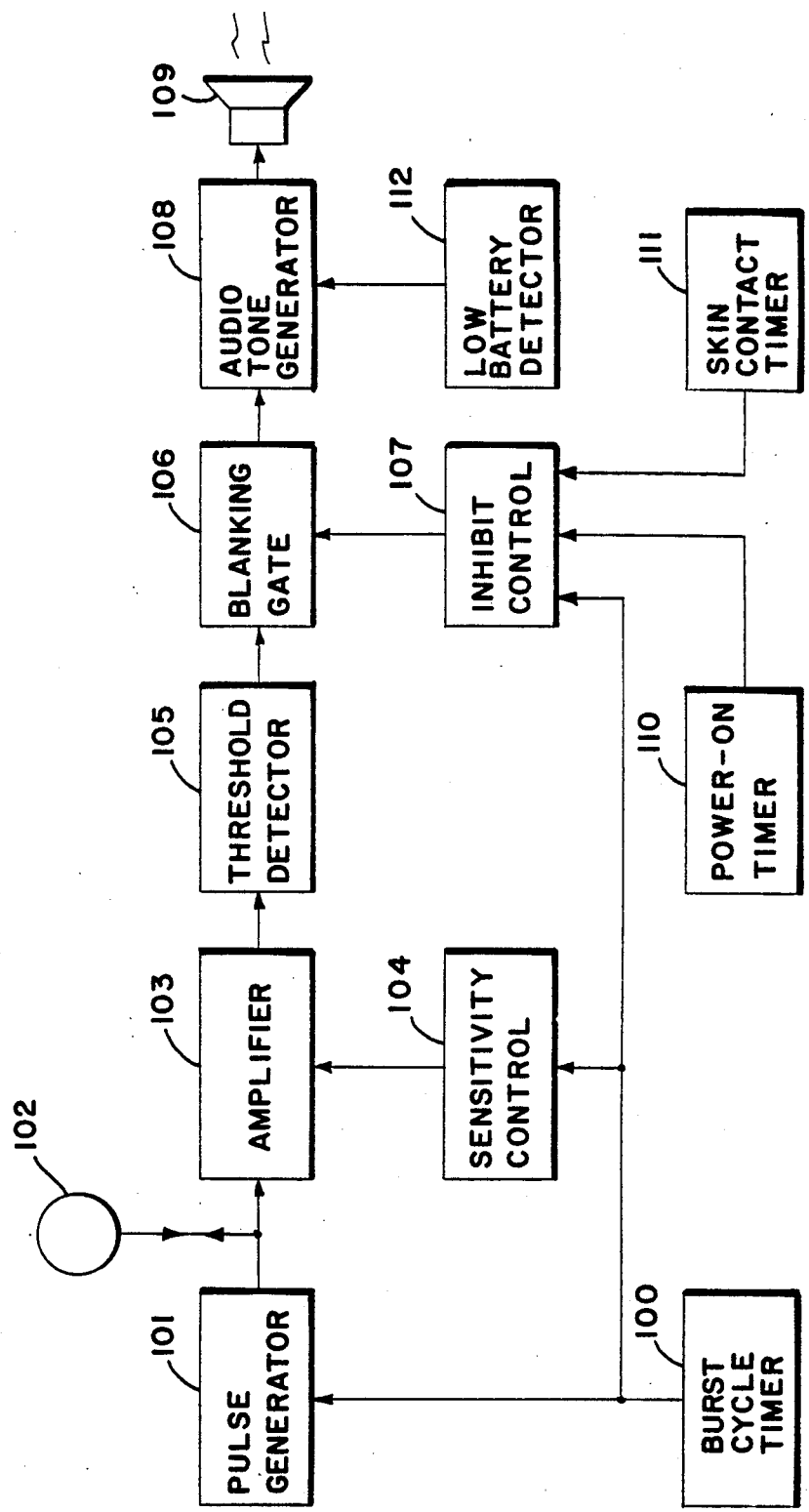
FIG. 2 is a block diagram of an ultrasonic detection device incorporating the present invention.

Referring now to the functional electronic block diagram of FIG. 2, the preferred embodiment of the present invention is shown. The improved ultrasonic detector is controlled primarily by a burst cycle timer 100. This burst cycle timer generates a pulse every 420 microseconds which is used to coordinate all of the activities of the various circuits in the ultrasound device. Burst cycle timer 100 drives the pulse generator 101 which initiates a pulse of energy to excite the ultrasonic piezoelectric transducer 102. The piezoelectric transducer generates an ultrasonic burst at approximately 1 MHz when excited by an energy pulse. This high frequency penetrates fluids quite well to provide adequate energy levels of reflections made by the fluid in the sow's uterus. The burst cycle timer 100 is implemented in the preferred embodiment by an industry standard 555 timer circuit. It will be appreciated by those skilled in the art that the burst cycle timer could also be implemented using astable multivibrators, crystal-controlled frequency synthesizers, or other frequency generators.

The quiet interval between the 420-microsecond bursts from the ultrasonic piezoelectric transducer 102 is monitored by amplifier 103 to detect reflections or echoes from the sow's uterus. Ultrasonic piezoelectric transducer 102 is capable of both transmitting and receiving energy. The amplifier in the preferred embodiment is very sensitive to returning echoes, since they may be quite attenuated by the time they are returned from the body of the sow. In order to ensure that the amplifier's sensitivity is not affected while the piezoelectric transducer is transmitting, a sensitivity control circuit 104 is included to reduce the sensitivity of amplifier 103 during the energy burst from the piezoelectric transducer 102. The timing of the sensitivity control circuit is controlled by the burst cycle timer 100.

The output of amplifier 103 is used to drive threshold detector 105. The amplifier output will include a pulse indicating initial ultrasonic energy transmission, a return echo pulse indicating the interface between the transducer and the animal's skin, and various other echo pulses from the internal organs of the animal. These pulses or echoes returning from the transducer 102 and amplified by the amplifier 103 are measured by the threshold detector circuit 105 against a preset threshold power level. Pulses that fall below the preset threshold are suppressed by threshold detector circuit 105. Only the energy pulses that rise above the minimum power threshold are passed from threshold detector circuit 105 to blanking gate 106. It has been shown by experience in the art that energy echoes from the sow's uterus will rise above a certain calculated threshold when the uterus is filled with amniotic fluid due to pregnancy. Therefore, echoes of sufficient energy force returning from the sow's uterus can be used to indicate pregnancy.

The purpose of blanking gate circuit 106 is to only pass pulses that arrive from threshold detector circuit 105 within calculated time windows occuring after the initial ultrasonic energy pulse is transmitted. Inhibit control circuit 107 drives the blanking gate circuit 106 and calculates the appropriate time window for use by blanking gate 106. The output of blanking gate circuit 106 is used to drive audio tone generator circuit 108. Any energy pulses within the appropriate time window that are passed by blanking gate circuit 106 will cause audio tone generator 108 to signal the user through sounder 109. In the preferred embodiment, the sounder 109 is implemented using a piezoelectric crystal sounder.

Inhibit control circuit 107 is driven by the burst cycle timer circuit 100, the power-on timer circuit 110, and the skin contact timer circuit 111. The purpose of the burst cycle timer circuit 100 in relation to the inhibit control circuit 107 is to coordinate the timing of the inhibit control signal used to drive blanking gate 106 with the transmission of the energy pulse out of pulse generator 101. Thus, inhibit control circuit 107 can prevent the transmitted energy pulse and the received skin-contact echo pulse from being passed to audio tone generator circuit 108 and causing a tone out of sounder 109. At the same time, the inhibit control circuit will allow the received echo pulses from the sow's uterus to pass through the blanking gate 106.

The purpose of power-on timer circuit 110 is to suppress the inhibit control signal sent by inhibit control circuit 107 to blanking gate circuit 106 for one-quarter second such that on initial power-up all transmitted energy pulses are passed by blanking gate circuit 106 to audio tone generator 108 to generate a tone out of sounder 109. Thus, upon power-up all circuits must operate in order to get a short chirp tone out of sounder 109, which verifies the correct operation of all circuits and components. The transducer need not be in contact with anything for the tone to be produced since it is triggered by the transmission energy pulse.

The purpose of skin contact timer 111 is to periodically shorten the inhibit control signal generated by inhibit control circuit 107 to allow the skin contact return echo received from transducer 102 to pass through blanking gate 106. The purpose of this is to verify the close contact between the transducer and the skin of the animal by monitoring the skin contact echo pulse. The inhibit control signal is normally approximately 150 microseconds in length to block both the transmitted energy pulse and the received skin contact echo pulse. The skin contact timer circuit shortens the inhibit control signal from approximately 150 microseconds to approximately 40 microseconds but does not eliminate the control signal in the fashion that the power-on timer circuit 110 does. The inhibit control signal is only shortened such that the inhibit control pulse continues to suppress the transmitted energy pulse from passing through blanking gate 106 but allows the skin contact echo pulse to pass to audio tone generator circuit 108. Skin contact timer circuit 111 is set to a cycle time of approximately two and one-half seconds such that the skin contact echo will be passed to audio tone generator circuit 108 for approximately 50 milliseconds on that periodic basis. Thus, every two and one-half seconds the user will hear a 50-millisecond tone sounding like a chirp representing the skin contact echo which will verify the good contact between the transducer and the animal's skin.

Inhibit control circuit 107 has three modes of operation. In its most general mode of operation it generates an inhibit control pulse of sufficient length to blank out both the initial ultrasonic energy pulse and the skin contact echo pulse as received from blanking gate circuit 106. In its second mode of operation the inhibit control circuit generates a shortened blanking pulse such that its active length is long enough to blank out the initial ultrasonic energy pulse but not the skin contact echo pulse as received by blanking gate circuit 106. In its third mode of operation, inhibit control circuit 107 does not generate any inhibit control pulses such that all signals received by blanking gate 106 are passed.

These three modes of operation correspond to the various modes of operation of the overall ultrasonic detector. The first mode of operation corresponds to detecting pregnancy in sows such that only the echo pulses received from the body of the sow are passed to an audio tone generator. Any strong echo indicating a large body of amniotic fluid in the sow's uterus, which would indicate pregnancy, is passed to audio tone generator circuit 108 and the user is alerted. The second mode of operation of the inhibit control circuit 107 corresponds to the periodic skin contact check to alert the user that good transducer-to-skin contact has been made. The period of the skin contact check is approximately two and one-half seconds, and a good transducer-to-skin contact is indicated by a short audible chirp by the ultrasonic detector alerting the user to proper operation of the device. The third mode of operation of the inhibit control circuit 107 is to verify correct operation of the overall circuit upon power-up. For approximately one-quarter second after initial power-up all inhibit control signals are suppressed to blanking gate circuit 106 such that all ultrasonic pulse transmissions are passed through blanking gate circuit 106 and alert the user through audio tone generator circuit 106 and sounder 109 of the correct operation of the circuit.

Low battery detector circuit 112 continually monitors the voltage level of the batteries in the ultrasonic detector. If the battery voltage drops below a preset margin, the low battery detector circuit 112 will indicate this condition to audio tone generator circuit 108, which will warn the user through sounder 109.

Audio tone generator 108 is the audible indicator means for alerting the user of various conditions of the circuit and for alerting the user as to the presence of pregnancy in the sow. In the preferred embodiment, audio tone generator 108 drives a piezoelectric sounder 109 which is used for tone output. The output pulse of the audio tone generator 108 is an extended 180-microsecond pulse of energy triggered by any pulse coming from blanking gate 106. The timing of the overall circuit, which in the preferred embodiment is set to a cycle time of 420 microseconds, has been selected in this preferred embodiment to coincide with the resonant frequency of the piezoelectric sounder and also to coincide with the amount of time it generally would take to receive an echo pulse from the sow's uterus. A 420-microsecond cycle time for the entire circuit corresponds to 2381 Hz frequency, which will produce a maximum volume output from piezoelectric sounder 109. It will be appreciated by those skilled in the art that the selection of tone output devices and the selection of operational frequency of the overall circuit is a matter of designer choice and can be varied without departing from spirit or scope of the present invention.

Figure 3:
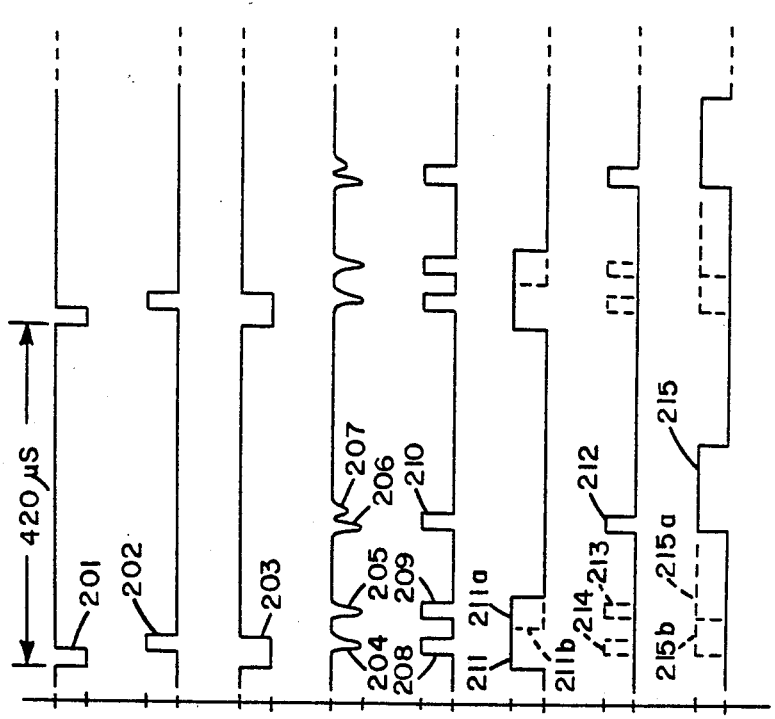
FIG. 3 is a timing diagram illustrating two cycles of operation of the circuit of FIG. 2.

The operation and coordination of control in the aforementioned circuits are better understood by reference to FIG. 3 in combination with FIG. 2. Line A of FIG. 3 shows the 420-microsecond cycle frequency of the burst cycle timer. This is the main control frequency distributed by the burst cycle timer circuit 100 shown in FIG. 2. This frequency is used to control and coordinate the activities of the various ultrasonic detector circuits. The pulse generator circuit 101 generates a pulse of energy 202 for piezoelectric transducer 102 following the burst cycle timer pulse 201 as shown in lines A and B of FIG. 3. The burst cycle timer circuit 100 also reduces the sensitivity of amplifier 103 for approximately 20 microseconds during the pulse generator operation by means of sensitivity control circuit 104. The sensitivity control circuit output reduces the sensitivity of amplifier 103 by means of a sensitivity reduction signal 203 shown in line C of FIG. 3. Note that the sensitivity control circuit 104 reduces the sensitivity of the amplifier 103 at the beginning of the burst cycle timer pulse and maintains the sensitivity at a reduced level until after the pulse generator has stopped applying energy to piezoelectric transducer 102. In this fashion the amplifer sensitivity is not overwhelmed by the high energy output of pulse generator 101.

Referring again to FIG. 2, the output of amplifier 103 is used to drive a threshold detector 105. The purpose of the threshold detector is to monitor the pulses amplified by amplifier circuit 103 and to indicate by means of an output signal when an energy pulse is received which rises above a predetermined or preset threshold. It has been shown by experience in the art that energy echoes from the sow's uterus will rise above a certain calculated threshold when the uterus is filled with amniotic fluid due to pregnancy. Therefore, echoes of sufficient energy force returning from the sow's uterus can be used to indicate pregnancy.

Referring to FIG. 3, the amplifier output is shown on line D. Initial pulse 204 shown on line D is the energy burst output of the pulse generator, after it has been attenuated by the reduced sensitivity of the amplifier during transmission of the ultrasonic energy pulse. Pulse 205 shown on line D of the amplifier output is an echo generated by the transducer-to-skin interface when the transducer is sufficiently close to the sow's skin. This echo would be absent if a good transducer-to-skin contact was not maintained. Echo 206 shown on line D of the amplifier output is indicative of a large body of amniotic fluid in the sow's uterus. Echo pulse 207 is a spurious reflection of a lower energy level which may indicate the backside interface between the amniotic fluid sac in the uterus, or some other density interface.

The pulses on the amplifier output shown on line D are fed to the threshold detector 105 which will output a pulse if the amplifier output rises above the minimum threshold required for pregnancy detection. The output threshold detector is shown on line E of FIG. 3 indicated by pulses 208, 209 and 210. It can be seen from the diagrams that the output pulse 208 from the threshold detector corresponds to the amplifier output 204. Threshold detector output pulse 208 therefore indicates the initial ultrasonic energy pulse output from the pulse generator 101. Threshold detector output pulse 209 corresponds to amplifier output pulse 205. Threshold detector output pulse 209 therefore indicates the echo from the piezoelectric transducer-to-skin interface. Output pulse 210 from the threshold detector corresponds to amplifier output pulse 206 which indicates the reflected echo from the uterus of the sow. Note that output pulse 207 from the amplifier does not rise to the threshold set by the threshold detector circuit 105 and hence does not produce an output pulse from the threshold detector as shown in line E.

The inhibit control circuit 107 receives signals from the burst cycle timer shown in FIG. 3 as line A, which triggers the inhibit control signal shown on line F of FIG. 3. The inhibit control signal 211 is initiated by the burst cycle timer pulse 201. The length of the inhibit control signal is approximately 150 microseconds and is calculated to remain active until after the ultrasonic transmission pulse 208 and the skin contact return echo pulse 209 have been received by the blanking gate 106 from the threshold detector 105. The portion of inhibit control signal 211 indicated as 211a extends to remain active longer than threshold detector output pulse 209 is active. The result is that the output of blanking gate circuit 106 remains inactive while inhibit control circuit 107 output is active, as shown in line G of FIG. 3, and only the return echo pulse 210 from the body of the sow is passed through blanking gate 106, as indicated by blanking gate output pulse 212. Blanking gate output pulse 212 triggers the audio tone generator circuit 108 to generate a momentary tone pulse 215 as shown on line H of FIG. 3. This pulse 215 is only approximately 180 microseconds long but a series of them will generate a tone of approximately 2381 Hz out of sounder 109.

The length of inhibit control signal 211 is periodically shortened by skin contact timer 111 as shown by the dotted portion 211b of signal 211 on line F of FIG. 3. The inhibit control signal 211 when shortened by portion 211b allows the skin contact echo pulse 209 of the threshold detector circuit 105 to be passed to audio tone generator 108 but continues to suppress the transmitted ultrasound pulse 208. Threshold detector output pulse 209, which represents the skin contact echo pulse 205, is passed through blanking gate 106 as shown as the dotted blanking gate output pulse 213. The period of the skin contact timer is set to be approximately two and one-half seconds such that the skin contact echo is allowed to pass through blanking gate circuit 106 for 50 milliseconds. This will cause the audio tone generator to emit a 50-millisecond chirp tone signal every 2.5 seconds out of piezoelectric sounder 109, indicating good skin contact, as shown by the dotted portion 215a of signal 215. When the ultrasonic detector circuit is being used, the operator is trained to listen for the skin contact chirp output of piezoelectric sounder 109 every two and one-half seconds, indicating a good transducer-to-skin contact. The absence of this chirp sound coming from piezoelectric sounder 109 would alert the user that a poor transducer-to-skin contact exists. This is a helpful signal to raise the confidence level of the user of the ultrasonic detection device to indicate proper operation of the device. As often is the case, the ultrasonic detector device will be used on a sow that is not pregnant and the device would not detect pregnancy in the sow, and hence the user would hear nothing from piezoelectric sounder 109. In order to inform the user that the circuit is operating properly even though no pregnancy is indicated, the two and one-half second skin contact chirp will occasionally remind the user that the circuit is operating properly.

The power-on timer circuit 110, as shown in FIG. 2, also operates to control the inhibit control circuit 107. The purpose of the power-on timer circuit is to provide a power-up confidence signal to be sent to the user of the ultrasonic detection device to inform the user that the circuit is operating properly. When power is first applied to the device, the power-on timer circuit 110 completely eliminates the inhibit control pulse output for one-quarter of a second after power-up. With the complete elimination of inhibit control pulse 211 shown on line F of FIG. 3, the initial pulse generator output 204 will pass pulse 208 through blanking gate 106 to generate an audio tone output of piezoelectric sounder 109 through audio tone generator 108 as shown by the dotted blanking gate output pulse 214 on line G and the dotted portion of audio output tone 215b on line H of FIG. 3. This pass-through condition upon power-up will present a tone to the user for approximately one-quarter second, indicating proper power-up and operation of the ultrasonic detection circuit.

In addition to the aforementioned benefits and improvements in the preferred embodiment of the ultrasonic detection device, a low battery detection circuit 112, shown in FIG. 2, continually monitors the voltage level of the battery in the hand-held ultrasonic detection device. Should the voltage level drop below a minimally acceptable threshold voltage, the low battery detector circuit will indicate this condition to the audio tone generator circuit 108. This in turn will cause a tone to be generated on piezoelectric sounder 109 to indicate a low battery.

The present invention may be practiced as an apparatus or a method which performs in the manner described herein.

Numerous characteristics and advantages of the invention have been set forth in the foregoing description together with details of structure and function of the invention and the novel features thereof are pointed out in the appended claims. The disclosure, however, is illustrative only and changes may be made in detail, especially in matters of shape, size and arrangement of parts and choice of electrical components within the principle of the invention to the full extent of the broad general meaning of the terms in which the appended claims are expressed.

What is claimed is:

1. Ultrasonic sensing apparatus for measurements of animals' bodies, comprising:

means including a transducer adapted to be placed against the skin of an animal for transmitting ultrasonic energy bursts and for providing energy signals corresponding to said transmitted ultrasonic energy bursts and echo signals corresponding to return echoes from the body;

signal processing means including electrical measurement and detection means connected for receiving said energy signals and echo signals and for detecting and measuring features thereof corresponding to anatomical features within the animal's body and indicating means operatively connected to said electronic measurement and detection means for providing indications to an operator of characteristics of the detected or measured anatomical features;

gate means operatively connected to said signal processing means and selectively operable in a first mode to suppress energy signals and echo signals occurring in a time period during and immediately after each ultrasonic pulse and corresponding in time to transmitted energy bursts and return echoes from the skin of the animal respectively, and selectively operable in a second mode to suppress energy signals occurring in said time period, and selectively operable in a third mode to pass all energy signals and echo signals; and switching means connected for controlling said gate means for normally operating in said first mode so that said signal processing means may indicate characteristics of the detected or measured anatomical features with the body, and for periodically switching said gate means to said second mode so that said indicating means will provide the operator with an indication of effective skin contact by the transducer, and for switching said indicating means to said third mode so that said indicating means will provide the operator with an indication of proper operation of the entire circuit.

2. Ultrasonic sounding apparatus for measurements on animals, comprising:

first means including a transducer adapted to be placed against the skin of an animal, for periodically transmitting ultrasonic energy bursts and for receiving return echoes from the animal's body;

circuit means electrically connected to said first means and operable for (1) receiving and amplifying energy pulses and echo pulses corresponding to said transmitted ultrasonic energy bursts and said received return echoes, respectively, (2) suppressing said pulses which are lesser in magnitude than a predetermined level, and (3) gating said pulses so that selected ones of said pulses are blocked and selected other ones of said pulses are passed;

blanking control means operably connected to said circuit means and synchronously operable in a first mode for causing said circuit means to block energy pulses corresponding to the periodically transmitted ultrasonic energy bursts and to pass echo pulses occuring thereafter until the next succeeding energy pulse;

said blanking control means operable in a second mode for causing said circuit means to further block echo pulses occuring within a predetermined time interval after a transmitted ultrasonic energy burst and corresponding to reflected ultrasonic energy returned from the skin of the animal;

timing means operatively connected to said blanking control means for switching said blanking control means between said first and second modes; and indicator means electrically connected to said circuit means and operable for alerting the user of said apparatus of the presence of said pulses passed from said circuit means.

3. Apparatus according to claim 2 including power-up control means electrically connected to said blanking control means and operable for causing said blanking control means to operate in a third mode for causing said circuit means to allow all of said pulses to pass through to said indicator means for a fixed period of time after the power is applied to said ultrasonic sounding apparatus.

4. An ultrasonic sounding apparatus for measuring back fat and determining pregnancy in animals, comprising:

transducer means for transmitting ultrasonic energy bursts into the animal, for receiving ultrasonic echoes returned from the animal's skin and body, and for producing corresponding energy pulses and echo pulses, respectively, said transducer means adaptable to be placed against the skin of the animal;

circuit means electrically connected to said transducer means operable for amplifying said energy pulses and said echo pulses and further operable for passing said pulses that are greater in magnitude than a preset level to a blanking means;

said blanking means electrically connected to said circuit means for receiving said pulses from said circuit means and selectively operable to pass or block passage of said pulses;

blanking control means electrically connected to said blanking means operable in a first mode for causing said blanking means to block said energy pulses corresponding to the transmitted ultrasonic energy bursts;

said blanking control means normally operable in a second mode for causing said blanking means to further block echo pulses corresponding to the received ultrasonic echoes returned from the skin of the animal;

said blanking control means operable in a third mode for causing said blanking means to pass said energy pulses corresponding to the transmitted ultrasonic energy bursts for a fixed period of time after the power is applied to the ultrasonic sounding apparatus so that a self-test is performed;

indicator means electrically connected to said blanking means and operable for alerting the user of said apparatus of the presence of pulses passed from said blanking means;

control timer means electrically connected to said transducer means and operable for causing said transducer to transmit said ultrasonic energy bursts on a fixed periodic basis;

said control timer means further electrically connected to said blanking control means and operable to synchronize said blanking control means to the transmission of said ultrasonic energy bursts; and skin contact timer means electrically connected to said blanking control means and operable for periodically placing said blanking control means into said first mode of operation so that skin contact is periodically checked.

5. The apparatus according to claim 4 wherein said control timer means is further electrically connected to said circuit means and operable for causing said circuit means to amplify at a first level said energy pulses corresponding to said transmitted ultrasonic energy bursts and operable to amplify at a second level said echo pulses corresponding to said received ultrasonic echoes.

6. The apparatus according to claim 4 wherein said indicator means includes a low battery detection means for alerting the user when batteries of sdid ultrasonic sounding apparatus fall below an acceptable preset threshold voltage.

7. The apparatus according to claim 1 wherein said transducer means includes an ultrasonic piezoelectric transducer.

8. The method of detecting and automatically indicating pregnancy in animals, comprising the steps of:

(a) generating an ultrasonic energy pulse and transmitting said energy pulse into the body of an animal by means of a transducer placed on the animal's body;

(b) receiving return echo pulses from the animal's skin and return echo pulses from the animal's body produced in response to said transmitted energy pulse and passing said echo pulses along a common channel with said energy pulse;

(c) amplifying said energy pulse and said echo pulses on said common channel;

(d) testing the amplitude of said amplitude pulses against a predetermined amplitude to eliminate pulses below said predetermined level from said common channel;

(e) blocking said amplified echo pulses on said common channel that correspond to ultrasonic energy reflection on the animal's skin;

(f) blocking said amplified energy pulse on said common channel;

(g) generating an audible tone in response to receiving from said common channel an unblocked amplified pulse with an amplitude greater than said predetermined level whereby to normally audibly indicate detection of a pregnancy condition;

(h) repeating steps (a) through (g) and periodically skipping step (e) whereby an audible tone is generated when an unblocked amplified echo pulse corresponding to the ultrasonic energy reflected from the animal's skin is received from said common channel to automatically audibly indicate the close contact of said transducer to the animal's skin; and (i) repeating steps (a) through (g) and skipping steps (e) and (f) for the initial and the several following repetitions of steps (a) through (g) whereby an audible tone is generated when an unblocked amplified energy pulse corresponding to the transmitted energy pulse is received to automatically audibly indicate that the steps are being performed properly without failure.

* * * * *

UNITED STATES PATENT AND TRADEMARK OFFICE
CERTIFICATE OF CORRECTION

PATENT NO. : 4,700,711
DATED : October 20, 1987
INVENTOR(S) : David L. Carlson

It is certified that error appears in the above-identified patent and that said Letters Patent is hereby corrected as shown below:

In column 11, line 31, change "sdid" to --said--.

In column 11, line 34, change "1" to --4--.

In column 12, line 16, change "reflection" to --reflected--.

Signed and Sealed this

Tenth Day of May, 1988

*Attest:*

DONALD J. QUIGG

*Attesting Officer*     *Commissioner of Patents and Trademarks*